US00PP16073P2

(12) United States Plant Patent
Olesen et al.

(10) Patent No.: US PP16,073 P2
(45) Date of Patent: Oct. 25, 2005

(54) ***CLEMATIS* PLANT NAMED 'EVIPO034'**

(50) Latin Name: *Clematis viticella*
Varietal Denomination: Evipo034

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 78 days.

(21) Appl. No.: 10/897,921

(22) Filed: Jul. 23, 2004

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses. With a tall growth habit, profuse, nodding violet and white flowers, continuous summer flowering and good disease resistance. The variety successfully propagates from softwood cuttings and is suitable for cultivation in commercial glasshouses. This new and distinct variety has shown to be uniform and stable in the resulting generations from asexual propagation.

3 Drawing Sheets

Botanical classification: *Clematis l.* Genus—*Clematis*. Species—*viticella.*
Variety denomination: 'Evipo034'.

SUMMARY OF THE DISCOVERY

The present invention constitutes a new and distinct variety of *Clematis* which originated as a chance seedling of unknown parents. The new variety is named 'Evipo034'.

The objective of the selection of this *Clematis* variety for commercial glasshouse and nursery culture was to create a new and distinct variety with unique qualities that this variety has:

1. Profuse nodding violet and white flowers;
2. Reliable and repeatable production plant;
3. Summer flowering;
4. Good disease resistance.

These qualities required improvement in *Clematis* varieties that were in commercial cultivation and the objectives have been substantially achieved in the new variety, as evidenced by the unique combination of characteristics that are present in 'Evipo034', which distinguish it from all other varieties of which we are aware.

Evaluations of the seedling plant were conducted in a controlled environment. As a result, 'Evipo034' was selected by Raymond J. Evison and Mogens N. Olesen in their *Clematis* development program in Domarie Vineries Les Sauvagees, St. Sampsons, Guernsey, Channel Islands, United Kingdom in June 1996.

Asexual reproduction of 'Evipo034' by cuttings was first done by Raymond J. Evison and Mogens N. Olesen in Domarie Vineries Les Sauvagees, St. Sampsons, Guernsey, Channel Islands, United Kingdom in April 1997. This initial and subsequent asexual propagations have demonstrated that the characteristics of 'Evipo034' are true to type and are transmitted from one generation to the next.

BRIEF DESCRIPTION OF THE DRAWING

The accompanying color illustrations show as true as is reasonably possible to obtain in color photographs of this type:

FIG. 2.2 Flower bud closed and ¼ open;

FIG. 2.3 Stem showing attachment of mature and juvenile leaves;

DETAILED DESCRIPTION OF THE VARIETY

Figure 1:
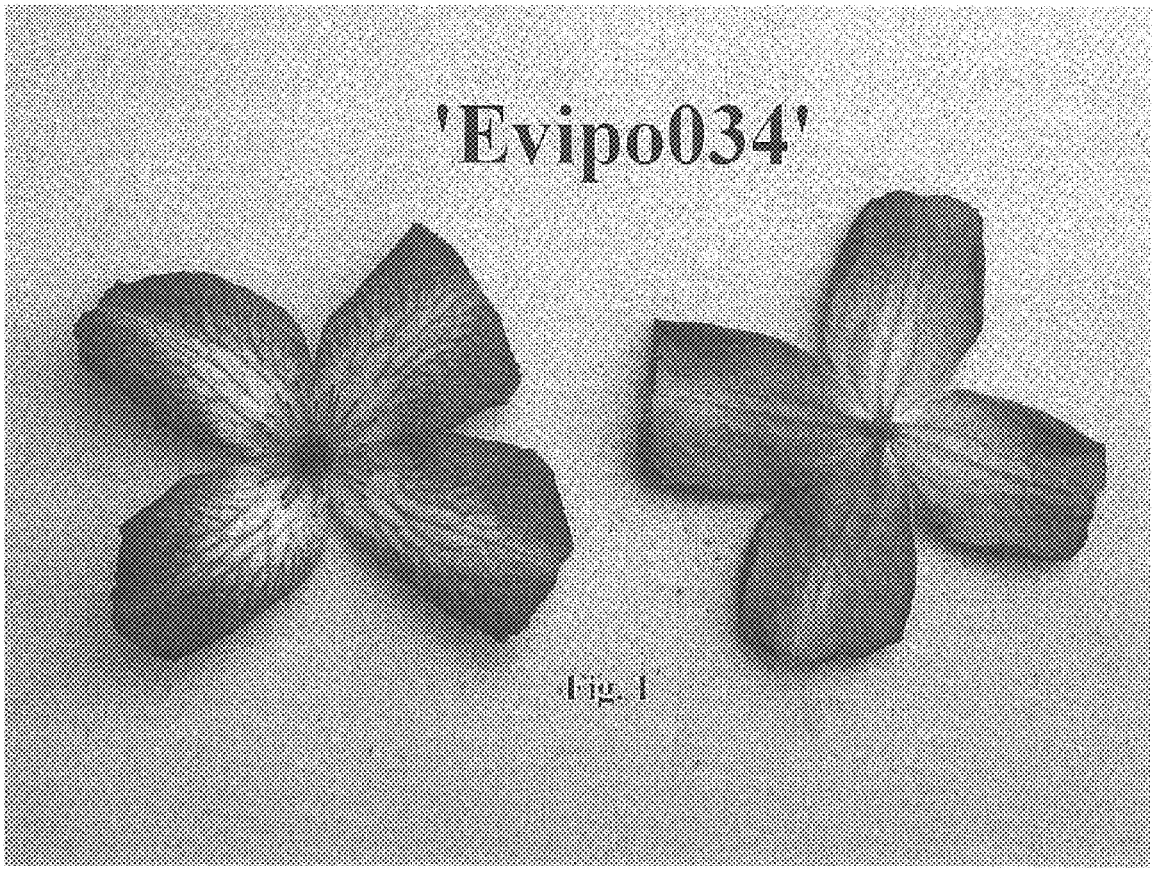
FIG. 1 Enlarged image of open flower, upper and lower surface.

The follwing is a detailed description of 'Evipo034', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Minuet', a non-patented variety. Chart 1 details several physical characteristics of 'Evipo034' and the comparison variety.

CHART 1

| | 'Evipo034' | 'Minuet' |
|---|---|---|
| Tepal upper color | White Group N155A at the base with tepal apex and margin violet Group 86D. | White Group N155A at the base with tepal apex and margin Purple Group N78A. |
| Flower | Above average for cultivar type. | Average for cultivar type. |

FLOWER AND FLOWER BUD

Blooming habit: Summer flowering. Normal flowering months are May, June, July, August, September.

Flower bud:

*Size.*—20 to 25 mm in length. Bud diameter is 6 to 8 mm.

*Bud form.*—Ovate.

*Bud texture.*—Pubescent.

*Bud color.*—Violet Group 85C, Green Group 140B at ¼ opening.

Peduncle:

*Aspects.*—Horizontal and facing downwards (nodding).

*Surface.*—Smooth and pubescent.

*Length.*—110 to 120 mm average length.

*Color.*—Green Group 141C turning to Purple Group N79C as the flower opens.

*Strength.*—Weak.

Receptacle: Absent.

Flower arrangement:

*Location on vine.*—Flowering normally occurs on new growth.

*Borne.*—Compound cyme cluster of 3 to 5 flowers.

Flower bloom:

*Size.*—50 to 55 mm in diameter. 12 mm in depth.

*Profile.*—Upon opening: Flowers are flat. After opening: Flowers are flat.

*Tepal color.*—Upon opening: Upper surface of tepal base is White Group N155A with tepal apex and margin Violet Group 86B in color. After opening: Upper surface of tepal base is White Group N155A in color with tepal apex and margin of Violet Group 86D in color. Lower surface has a middle zone of White Group N155A with the outer margin region a similar color to the upper but slightly lighter tending toward Violet Group 85A.

*Variations.*—Tepal veins are Violet Group 86C. Tepal apex turns Red-Purple Group 70A as the tepals age.

*Fragrance.*—None.

*Lasting quality on plant.*—10 to 15 days.

*Lasting quality as a cut flower.*—4 to 5 days.

Tepals:

*Quantity.*—Normally 4 tepals, rarely 5 tepals observed.

*Size.*—26 to 33 mm in length by 17 to 20 mm wide.

*Shape.*—Individual tepal shape is obovate.

*Undulation of margin.*—Weak and weakly serrated.

*Tepal apex.*—Truncate.

*Recurvature of tip.*—Absent.

*Persistence.*—Tepals hang on and dry.

*Arrangement.*—Tepals are arranged regularly.

Reproductive organs:

*Arrangement.*—Open.

*Pollen.*—Quantity: Below average. Color: Yellow Group 8D.

*Anthers.*—Size: 4 to 5 mm in length. Color: Greyed-Yellow Group 160D. Tips of anthers are Purple Group N77 in color. Quantity: 20 to 30.

*Filaments.*—Color: Yellow-Green Group 150C. Length: 6 mm.

*Pistils.*—Quantity: 24 to 32.

*Stigmas.*—Inferior to anthers, becoming superior as the flower opens.

*Styles.*—Color: Purple Group 79B. Length: 9 to 11 mm.

Seed head characteristics: None observed. Self-pollination appears rarely.

PLANT

Plant form: Climbing.

Size: Seasons growth attains 2.5 to 3 meters in height. Average spread is 1 to 1.5 meters.

Hardiness: Trials to date show the variety hardy in USDA Zones 3–9.

Stems:

*Color.*—Young wood: Yellow-Green Group 150D. Older wood: Greyed-Orange N167B.

*Internodes.*—Shape: Cylindrical. Length: 120 to 160 mm.

*Surface.*—Young wood: Smooth. Older wood: Smooth.

Plant foliage:

*Leaf characteristics.*—Deciduous.

*Mature leaf form.*—Normally trifoliate but often up to 5 to 7 leaflets arranged in pinnate form. Average leaflet count of 3 to 5.

*Compound leaf size.*—150 mm (l)×115 mm (w).

*Abundance.*—Generally there are 12 leaves per 150 mm of stem.

*Color.*—Upper surfaces of mature leaves: Green Group 143B. Lower surfaces of mature leaves: Green Group 143D. Upper surfaces of new foliage: Green Group 143B. Lower surfaces of new foliage: Yellow-Green Group 141D.

Plant leaves and leaflets:

*Stipules.*—Absent.

*Petioles.*—Average length: 42 to 60 mm. Color: Yellow-Green Group 145B. Clasping: By leaf petiole.

*Petioloule.*—Length: 5 to 15 mm. Color: Yellow-Green Group 145B.

*Leaflet shape.*—General shape: Oval to elliptic. Base: Rounded. Apex: Rounded to acute. Margin: Entire.

*Leaflet size.*—25 to 30 mm in length by 15 to 25 mm wide.

*Leaflet texture.*—Upper side: Smooth. Lower side: Smooth. Pubescent: No. Thickness: Moderate. Glossiness: Moderately Glossy Finish.

Disease resistance: Subject to any disease that normally attacks the species, however the variety is more tolerant to Botrytis, *Phoma clematadina,* and root diseases such as Theilaviopsis than some *Clematis.*

We claim:

1. A new and distinct variety of *Clematis* plant named 'Evipo034', described and illustrated herein, due to its abundant nodding violet and white flowers, attactive long-lasting foliage and repeatable flowering under glasshouse conditions, suitability for production from softwood cuttings in pots, durable flowers and foliage which make the variety suitable for distribution in the floral industry.

* * * * *

Figure 2:
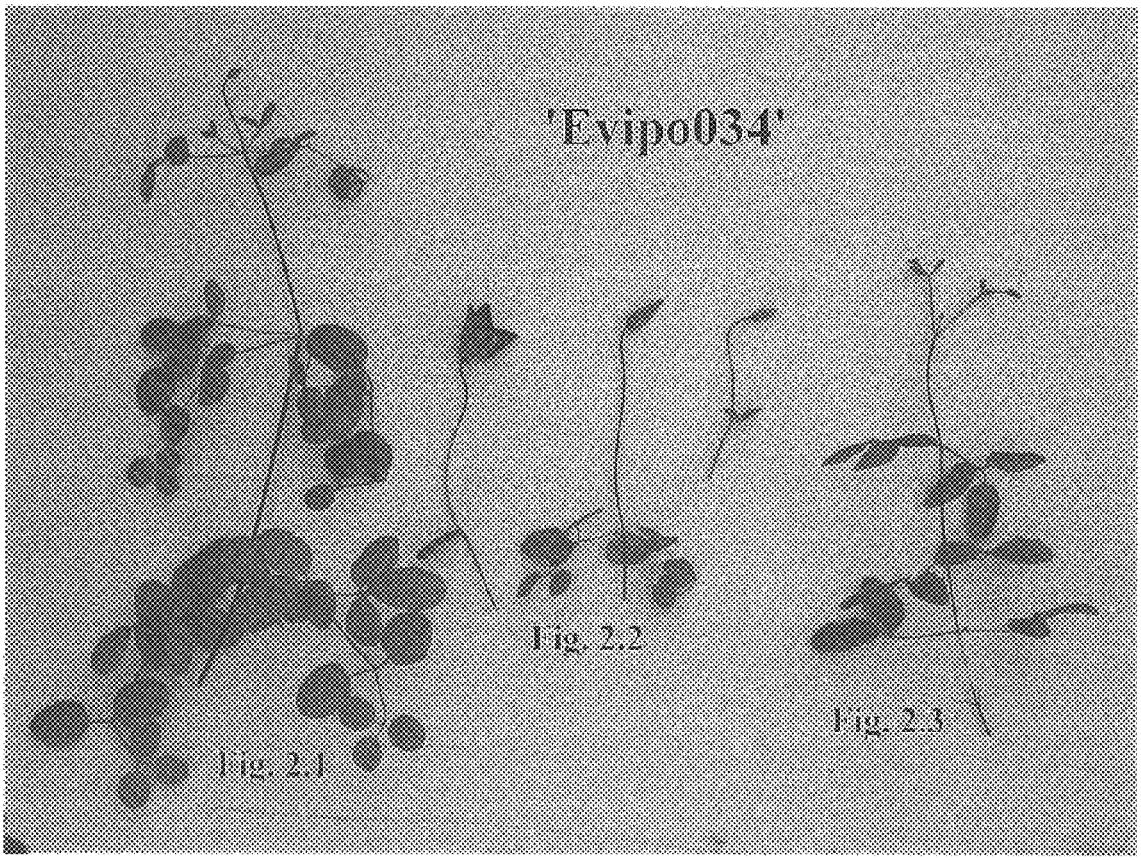
FIG. 2.1 Stem showing branching and the attachment of leaves.
Figure 3:
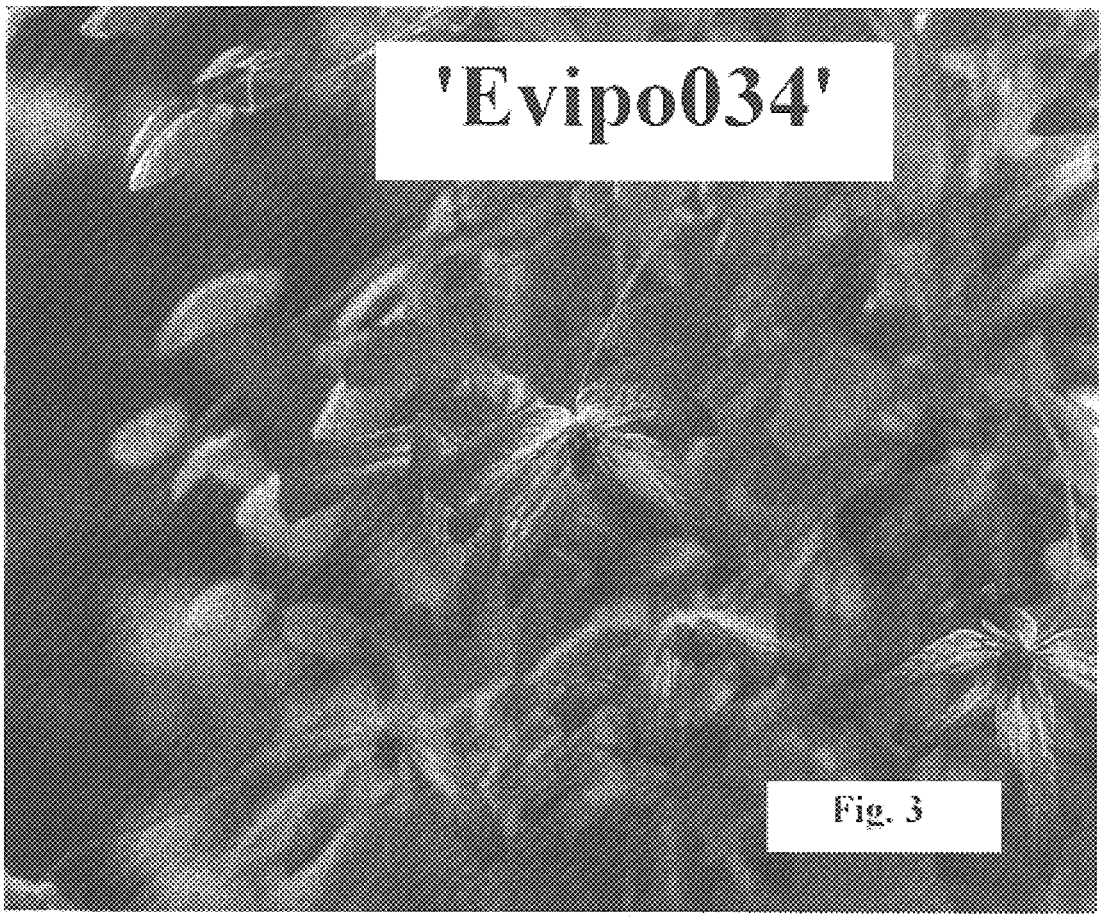
FIG. 3 Cluster of flowers showing attitude.

'Evipo034'
Fig. 2.1
Fig. 2.2
Fig. 2.3